Figure 1:
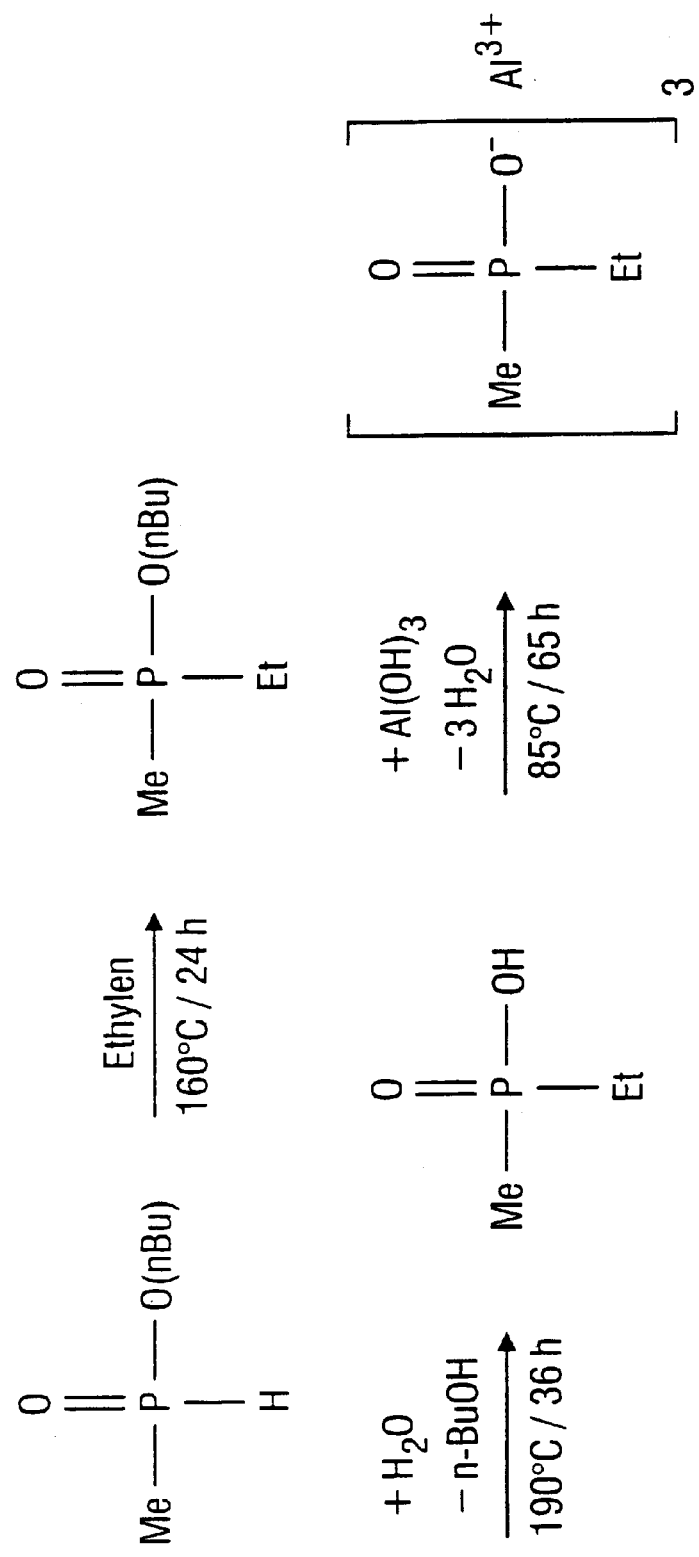

United States Patent [19]

Seitz

[11] Patent Number: 6,096,914

[45] Date of Patent: Aug. 1, 2000

[54] METHOD FOR PRODUCING ALUMINUM PHOSPHINATES

[75] Inventor: Thomas Seitz, Heddesheim, Germany

[73] Assignee: Ticona GmbH, Germany

[21] Appl. No.: 09/269,434

[22] PCT Filed: Sep. 24, 1997

[86] PCT No.: PCT/EP97/05228

§ 371 Date: Mar. 26, 1999

§ 102(e) Date: Mar. 26, 1999

[87] PCT Pub. No.: WO98/13371

PCT Pub. Date: Apr. 2, 1998

[30] Foreign Application Priority Data

Sep. 27, 1996 [DE] Germany .......................... 196 39 657

[51] Int. Cl.[7] ........................................... C07F 9/30
[52] U.S. Cl. .................................. 556/14; 562/8
[58] Field of Search .................... 556/14; 562/8

[56] References Cited

U.S. PATENT DOCUMENTS 3,563,948  2/1971  Spivack et al. .
4,272,448  6/1981  Bernard et al. .
4,972,011  11/1990  Richardson et al. .

FOREIGN PATENT DOCUMENTS 245207  11/1987  European Pat. Off. .
1558606  of 0000  France .
2017706  10/1979  United Kingdom .

*Primary Examiner*—Michael G. Ambrose
*Attorney, Agent, or Firm*—Connolly, Bove, Lodge & Hutz LLP

[57] ABSTRACT

This invention relates to a method for producing aluminum phosphinates of the formula $[R_1R_2P(O)O^-]_3Al^{3+}$, where $R_1$ and $R_2$ are the same or different and represent a $C_{1-8}$ alkyl group or a phenyl group. The process involves reaction of the corresponding alkali metal phosphinate with aluminum sulfate. The aluminum phosphinate salts are useful as a flame retardant for plastics.

12 Claims, 2 Drawing Sheets

Stand der Technik

METHOD FOR PRODUCING ALUMINUM PHOSPHINATES

The present invention relates to a process for preparing aluminum salts of dialkylphosphinic acids.

The aluminum salts of dialkylphosphinic acids (also referred to as aluminum phosphinates below) have increasing industrial importance as flame retardants for plastics and plastic molding compositions. In particular, they are an alternative for the halogen-containing flame retardants used hitherto, which, because of their halogen content, have corrosive effect and also have ecological disadvantages.

Processes for preparing aluminum phosphinates have already been described. For example, N. M. Karayannis et al. in Transition Met. Chem., 6, 79–82 (1981) discloses a process for preparing the aluminum salt of methylphenylphosphinic acid, in which methyl methylphenylphosphinate is reacted with anhydrous aluminum chloride. However, a large excess of methyl ester is required here, and stoichiometric amounts of the ecologically questionable methyl chloride are produced. A further disadvantage is that the chloride ions have a corrosive action on the steel equipment which is usual in industry. In addition, some of the chloride ions can remain in the aluminum phosphinate which is produced, and this can give problems when it is used, because the chloride ions have corrosive action.

French Patent 1,558,606 describes a process for preparing aluminum alkylhydroxyphenylalkylphosphinate from the corresponding alkali metal salt, the reaction likewise using aluminum chloride.

It is also known that aluminum phosphinates can be prepared (EP-A-0 699 708) by neutralization of the corresponding phosphinic acids with a suspension of aluminum hydroxide in water.

However, this process requires a very long reaction time and is therefore complicated and expensive for preparation on an industrial scale; this greatly reduces the possibilities for use of the products as flame retardants for plastics. For example, the reaction time necessary for aluminum ethylmethylphosphinate, which is of particular interest as a flame retardant, is 65 hours at from 80 to 85° C. The phosphinic acids which are to be used as starting material are obtained by acid hydrolysis of phosphinic esters (DE-A-2 441 878, DE-A-2 441 783), and, for the preparation of ethylmethylphosphinic acid, this requires reaction temperatures of more than 180° C. over a period of more than 30 hours.

There has therefore been a need for a process for preparing aluminum dialkylphosphinates which allows the desired products to be obtained simply and in a short time, while avoiding ecologically questionable, chloride-containing starting materials and by-products.

According to the invention, it has now been found that aluminum phosphinates of the formula (I)

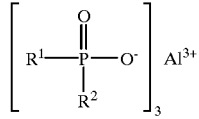

(I)

where $R^1$ and $R^2$ are identical or different and are linear or branched, $C_1$–$C_8$-alkyl, preferably $C_1$–$C_6$-alkyl, e.g. methyl, ethyl, n-propyl, isopropyl, n-butyl, iso-butyl, tert-butyl, n-pentyl or an isomer thereof, or n-hexyl or an isomer thereof, or phenyl, can be prepared in a simple and economical manner by reacting the corresponding alkali metal phosphinate of the formula (III)

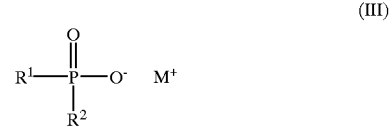

(III)

with aluminum sulfate.

In formula (III), $R^1$ and $R^2$ are as defined above and M is a metal of group I of the periodic table, M=sodium being particularly preferred.

FIG. 1 shows the process according to EP-A-0 699 708.

Figure 2:
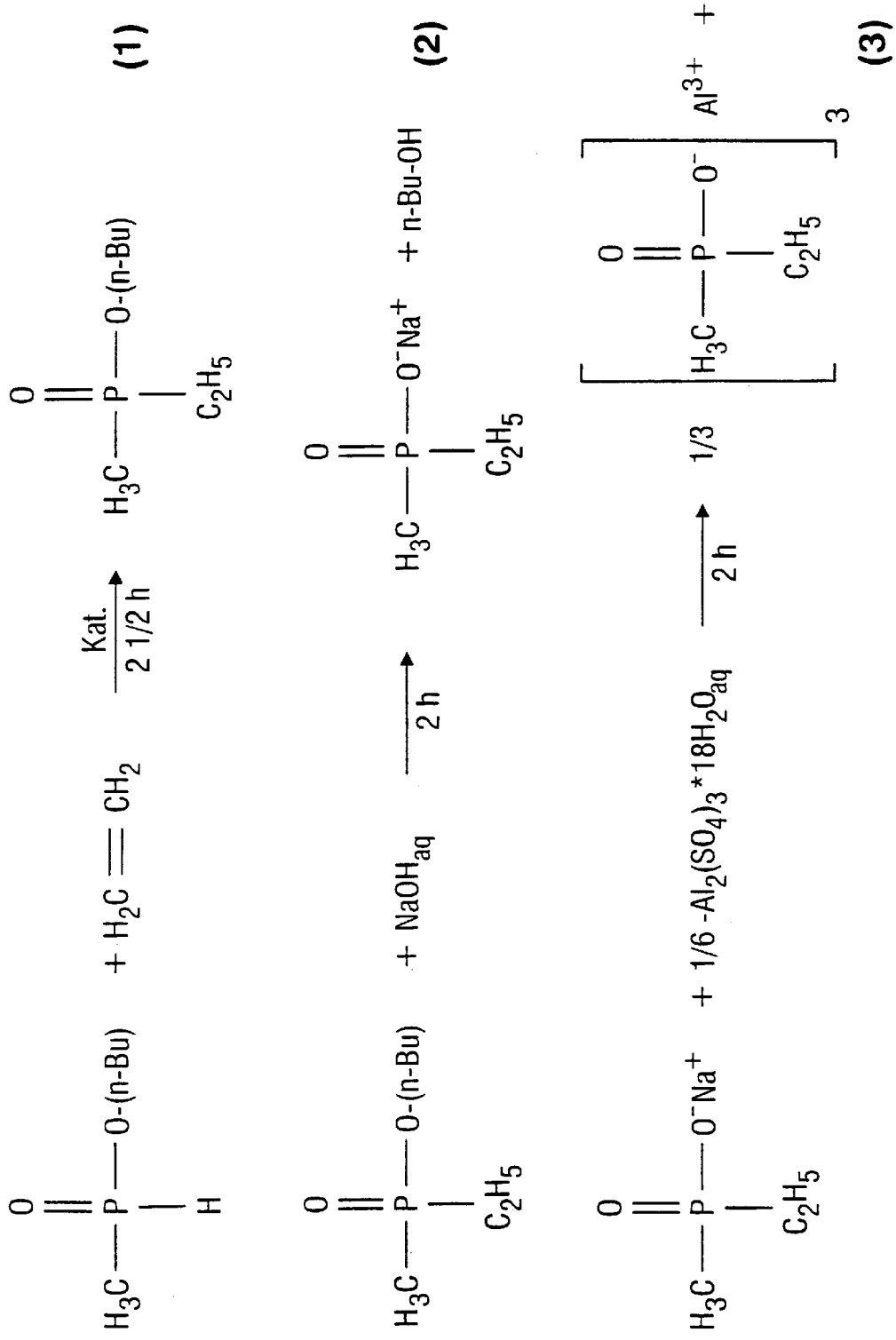

FIG. 2 shows the novel process (step 3) and the preparation of the precursors (steps 1 and 2).

The aluminum phosphinate of the formula (I) is formed by dropwise addition of the aluminum sulfate at a temperature of preferably from 20 to 27° C. (room temperature). Surprisingly, the product to be formed precipitates immediately during this procedure, so that the time of from about 10 minutes to 4 hours during which the dropwise addition continues corresponds to the reaction time. Continued stirring is unnecessary.

The aluminum phosphinates may be isolated by simple filtration and washing a number of times with water in order to remove any sulfate which may still be adhering to the product.

The amount of aluminum sulfate which is to be used is not of great significance. It is sufficient for the novel process to use a stoichiometric amount of ⅙ equivalent, based on the alkali metal phosphinate.

The solvent used may be any solvent in which the starting materials are soluble, but water is particularly preferred.

In order to obtain a good grain size in the product and thus good screening properties, it is advantageous to use a minimum amount of solvent of about 3.5 ml, based on 1 g of alkali metal phosphinate.

A further substantial advantage of the invention is that the synthesis of the alkali metal phosphinate of the formula (III) used as starting material and the following reaction thereof with aluminum sulfate to give the corresponding aluminum phosphinate can be carried out in a one-pot reaction without prior isolation and purification of the alkali metal phosphinate.

The alkali metal phosphinate of the formula (III) which is to be used as starting material may be obtained, for example, by a method based on the specification in J. Am. Chem. Soc. (1972), 94, 9260, by heating the corresponding phosphinate of the formula (II)

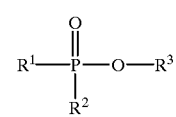

(II)

while adding an equivalent amount of aqueous alkali metal hydroxide solution, followed by (azeotropic) distillation of the water/alcohol ($R^3$—OH) mixture using a bath temperature of from 80 to 180° C., preferably from 100 to 150° C. $R^1$ and $R^2$ here are as defined above for formulae (I) and (III), and $R^3$ is alkyl having from 1 to 8 carbon atoms, preferably from 1 to 4 carbon atoms, very particular preference being given to $R^3$=n-butyl or isobutyl.

The reaction times for the saponification step are from 1 to 4 hours.

The yields in the novel process, based on the phosphinate of the formula (II) which is used, are virtually quantitative.

The phosphinate of the formula (II) may be prepared by a method based on the specification in DE-A-2 100 779, by free-radical addition of 1-olefins to the corresponding phosphonites. In this step also, it is unnecessary to isolate and purify the phosphinate of the formula (II) which is obtained, but rather these may be reacted in a one-pot synthesis, as described above, to give the corresponding alkali metal salts.

In summary, it should be made clear that the novel process is distinguished by considerably shortened reaction times and lower reaction temperatures, when comparison is made with the process described in EP-A-0 699 708. Furthermore, the novel process avoids the use of ecologically questionable halides as reaction partners, and also has the advantage that the synthesis of the precursors, and the actual reaction can be carried out as a one-pot synthesis without a separate step for isolation and purification of the respective precursors.

The novel process is illustrated below using selected examples.

EXAMPLE 1

Aluminum ethylmethylphosphinate

Under an atmosphere of argon, 312.5 g (2.5 mol) of 32% strength aqueous sodium hydroxide and 156 ml of water are added at 25° C., without interruption and with stirring, to 330.3 g (2.5 mol) of n-butyl ethylmethylphosphinate. The n-butanol/water mixture is distilled off azeotropically at 140° C. (boiling range: from 93 to 96° C.), the reflux ratio being adjusted so that after 2 h 15 min only pure water distils over. The resultant yellowish solution of sodium methylphosphinate is mixed with a further 936 ml of water. 277.7 g (0.42 mol) of aluminum sulfate octadecahydrate in 270 ml of water are added dropwise at 23° C. within a period of 2 hours, with stirring, and the product precipitates immediately. The resultant solution is filtered, and the residue is washed a number of times with water. Drying under reduced pressure at 150° C. gives 278.6 g of aluminum ethylmethylphosphinate (96% of theory) as a white powder (m.p. >380° C.).

EXAMPLE 2

Aluminum methyl-n-propylphosphinate

Under an atmosphere of argon, 324.7 g (2.6 mol) of 32% strength aqueous sodium hydroxide and 262 ml of water are added at 25° C., without interruption and with stirring, to 463.2 g (2.6 mol) of isobutyl methyl-n-propylphosphinate. The isobutanol/water mixture is distilled off azeotropically at 130° C. (boiling range: from 90 to 95° C.), the reflux ratio being adjusted so that after 2 h 15 min only pure water distils over.

The resultant yellow solution of sodium methyl-n-propylphosphinate is mixed with a further 1050 ml of water. 288.6 g (0.43 mol) of aluminum sulfate octadecahydrate in 300 ml of water are added dropwise at 23° C. within a period of 2 hours, with stirring, and the product precipitates immediately. The resultant solution is filtered, and the residue is washed a number of times with water. Drying under reduced pressure at 150° C. gives 330.0 g of aluminum methyl-n-propylphosphinate (99% of theory) as a white powder (m.p. >380° C.).

What is claimed is:

1. A process for preparing aluminum phosphinates of the formula (I)

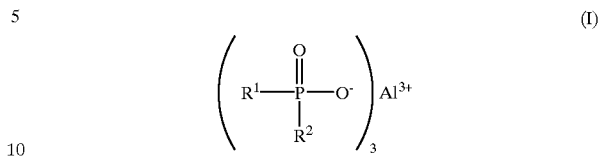

where $R^1$ and $R^2$ are identical or different and are linear or branched $C_1$–$C_8$ alkyl or phenyl, which comprises reacting alkali metal phosphinates of the formula (III)

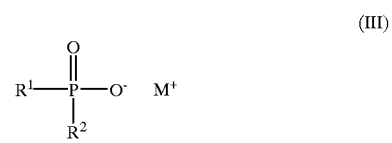

where $R^1$ and $R^2$ are as defined above and M is a metal of group I of the periodic table, with aluminum sulfate.

2. The process as claimed in claim 1, where $R^1$ and $R^2$ are methyl, ethyl, n-propyl, isopropyl, n-butyl, isobutyl, tert-butyl, n-pentyl or an isomer thereof, or n-hexyl or an isomer thereof.

3. The process as claimed in claim 1, where the alkali metal phosphinate of the formula (III) is prepared by saponification of a phosphinate of the formula (II) by adding aqueous alkali metal hydroxide

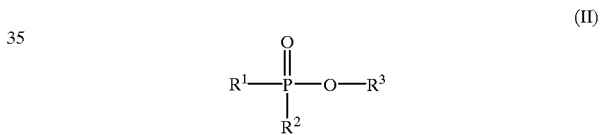

where $R^1$ and $R^2$ are as defined in claim 1 and $R^3$ is linear or branched $C_1$–$C_8$-alkyl, the alcohol which is produced being distilled off, and the resultant alkali metal phosphinate of the formula (III), without prior purification and/or isolation, is reacted in a one-pot synthesis with aluminum sulfate to give the corresponding aluminum phosphinate.

4. The process as claimed in claim 1, where the aluminum sulfate is used in a stoichiometric amount, based on the alkali metal phosphinate.

5. The process as claimed in claim 1, where the alkali metal phosphinate of the formula (III) is reacted with aluminum sulfate in an aqueous medium as solvent.

6. The process as claimed in claim 5, where water is used in an amount of at least 3.5 ml, based on 1 g of alkali metal phosphinate of the formula (III).

7. The process as claimed in, claim 1 where the alkali metal phosphinate of the formula (III) is reacted with aluminum sulfate at a temperature of from 20 to 27° C.

8. The process as claimed in, claim 1 where $R^1$ and $R^2$ are identical or different and are linear or branched $C_1$–$C_6$-alkyl or phenyl, $R^3$ is linear or branched $C_1$–$C_4$-alkyl, and M is sodium.

9. The process as claimed in claim 8, where $R^1$ and $R^2$ are methyl, ethyl, n-propyl, isopropyl, n-butyl, tert-butyl, n-pentyl or an isomer thereof or n-hexyl or an isomer thereof, R³ is n-butyl or isobutyl, and
M is sodium.

10. The process as claimed in claim 2, where the alkali metal phosphinate of the formula (III) is prepared by saponification of a phosphinate of the formula (II) by adding aqueous alkali metal hydroxide

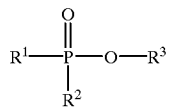
(II)

where R¹ and R² are as defined in claim 1 and R³ is linear or branched $C_1$–$C_8$-alkyl, the alcohol which is produced being distilled off, and the resultant alkali metal phosphinate of the formula (III), without prior purification and/or isolation, is reacted in a one-pot synthesis with aluminum sulfate to give the corresponding aluminum phosphinate.

11. The process as claimed in claim 10, where the aluminum sulfate is used in a stoichiometric amount, based on the alkali metal phosphinate.

12. The process as claimed in claim 11, where the alkali metal phosphinate of the formula (III) is reacted with aluminum sulfate in an aqueous medium as solvent.

* * * * *